United States Patent [19]

Iwashita et al.

[11] 4,301,144

[45] Nov. 17, 1981

[54] BLOOD SUBSTITUTE CONTAINING MODIFIED HEMOGLOBIN

[75] Inventors: Yuji Iwashita, Kawasaki; Katsumi Ajisaka, Yokohama, both of Japan

[73] Assignee: Ajinomoto Company, Incorporated, Tokyo, Japan

[21] Appl. No.: 167,360

[22] Filed: Jul. 10, 1980

[30] Foreign Application Priority Data

Jul. 11, 1979 [JP] Japan .................................. 54-87910

[51] Int. Cl.³ ...................... A61K 31/74; A61K 37/00
[52] U.S. Cl. ...................................... 424/78; 424/177; 260/112 R
[58] Field of Search ............... 424/177, 78; 260/112.5, 260/112 R

[56] References Cited

PUBLICATIONS

Sasakawa et al., Chem. Abst., vol. 77, (1972), p. 71989e.
Pace et al., Chem. Abst., vol. 79, (1973), p. 112553v.
Tam et al., Chem. Abst., vol. 85, (1976), p. 83209d.

*Primary Examiner*—Sam Rosen
*Attorney, Agent, or Firm*—Oblon, Fisher, Spivak, McClelland & Maier

[57] ABSTRACT

A novel modified hemoglobin was prepared. The hemoglobin is coupled with a polyalkylene glycol or its derivative, and the products are useful as a blood substitute. The oxygen-carrying capacity of this hemoglobin is nearly equal to that of a native hemoglobin, and the residence time in the circulation is satisfactorily long.

7 Claims, 2 Drawing Figures

BLOOD SUBSTITUTE CONTAINING MODIFIED HEMOGLOBIN

BACKGROUND OF THE INVENTION

1. Field of the Invention

This invention relates to a novel blood substitute containing a modified hemoglobin as an oxygen-carrying material.

2. Brief Description of the Prior Art

It is known to use a blood substitute containing hemoglobin free from stromal components as an oxygen-carrying material (S. F. Rabiner et al. J. Ex. Med., vol. 126, p 1142 (1967)). On the other hand, it is also known that when the hemoglobin is infused into the circulation, it is rapidly excreted through the kidney and metabolized by other metabolic routes. In order to solve this problem, various proposals have been made, for example, a hemoglobin crosslinked with glutaraldehyde (Japan KOKAI No. 76-63920), a hemoglobin coupled with dextran (Japan KOKAI No. 77-51016), and a hemoglobin combined with hydroxyethyl starch (German patent Offenlegungsschrift No. 2616086). However, in the first case, oxygen is difficult to transfer at tissue, because oxygen affinity of the hemoglobin is too tight. In case of the latter two proposals, high concentration of the hemoglobin often leads to unfavorable results because of its high viscosity.

SUMMARY OF THE INVENTION

It has now been found that when hemoglobin is combined with a polyalkylene glycol or its derivative (hereinafter referred to as "modified hemoglobin"), the oxygen-carrying ability of the modified hemoglobin is nearly equal to that of the original hemoglobin, and the residence time in the circulation is satisfactorily long.

DESCRIPTION OF THE PREFERRED EMBODIMENTS

The polyalkylene glycol and its derivative applicable to the invention include polyethylene glycol, polypropylene glycol, a copolymer of ethylene glycol and propylene glycol, an ether of one of the above-mentioned polyalkylene glycols and an alcohol having a carbon number of 1 to 16, such as monomethyl ether, monocetyl ether and monooleyl ether, an ester of one of the above polyalkylene glycols and a carboxylic acid having a carbon number of 2 to 18, such as monobutyl ester and monostearyl ester, and a dehydrated product of one of the above polyalkylene glycols and an amine having a carbon number of 1 to 18, such as propylamine and stearylamine. The above polyalkylene glycols and their derivatives are hereinafter referred to as "polymer employed in the invention". Molecular weight of the polymer employed in the invention is usually 300~20,000, preferably 750~5,000 in terms of elongation of residence time in circulation.

The hemoglobin applicable to the invention includes those of human, cow, swine, sheep, horse, dog, monkey, rabbit, and hen.

The hemoglobin and the polymer employed in the invention may be coupled by any means, and for example, they are directly combined using a condensing agent such as cyanogen bromide, or they are combined using a cross-linking reagent such as cyanuric chloride, 2,2'-dichlorobenzidine, p,p'-difluoro-m,m'-dinitrodiphenylsulfone and 2,4-dichloronitrobenzene. 4 to 120 molecules of the polymer employed in the invention are combined to one hemoglobin molecule.

The modified hemoglobin may be prepared according to the following methods:

(1) Polyethylene glycol is reacted with 2 to 5 times moles, preferably 3 times moles of cyanogen bromide at pH 9-10. Residual cyanogen bromide is removed from the reaction mixture by gel filtration, dialysis, etc., and then the product is reacted with 1/10–1/500 time mole, preferably 1/50–1/100 time mole of hemoglobin at pH 7–9, preferably 7.5–8 in an aqueous solution.

(2) Polyethylene glycol is added to benzene containing excess amount of sodium carbonate, and reacted with 2-5 times moles, preferably 3-4 times mole of cyanuric chloride. The reaction product of polyethylene glycol-4,6-dichloro-S-triazine is then separated, and reacted with 1–1/500 time mole, preferably 1/10–1/100 time mole of hemoglobin in a buffer solution of pH 8–9.5.

The above methods are also applicable to other polymers employed in the invention.

Figure 1:
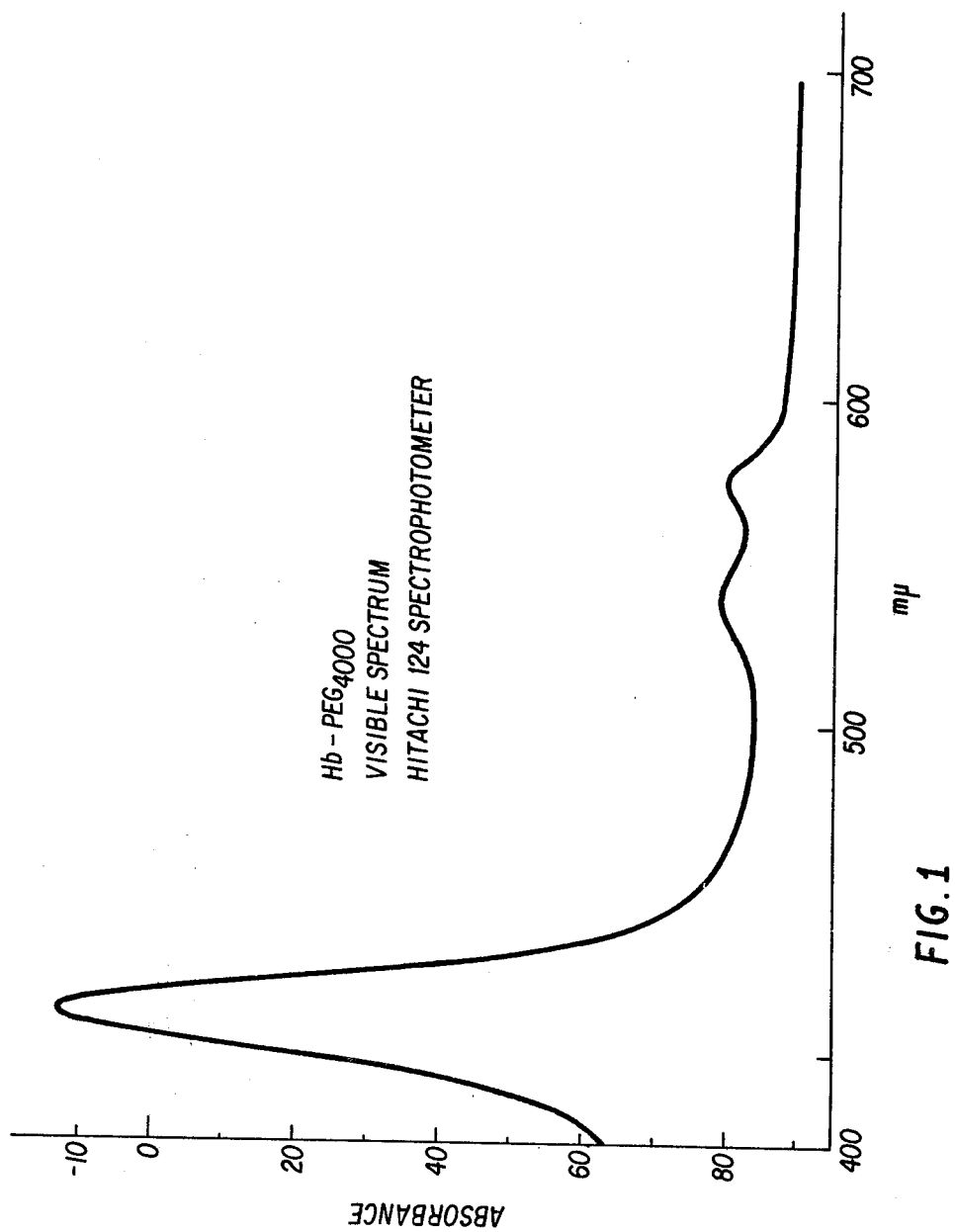
Figure 2:
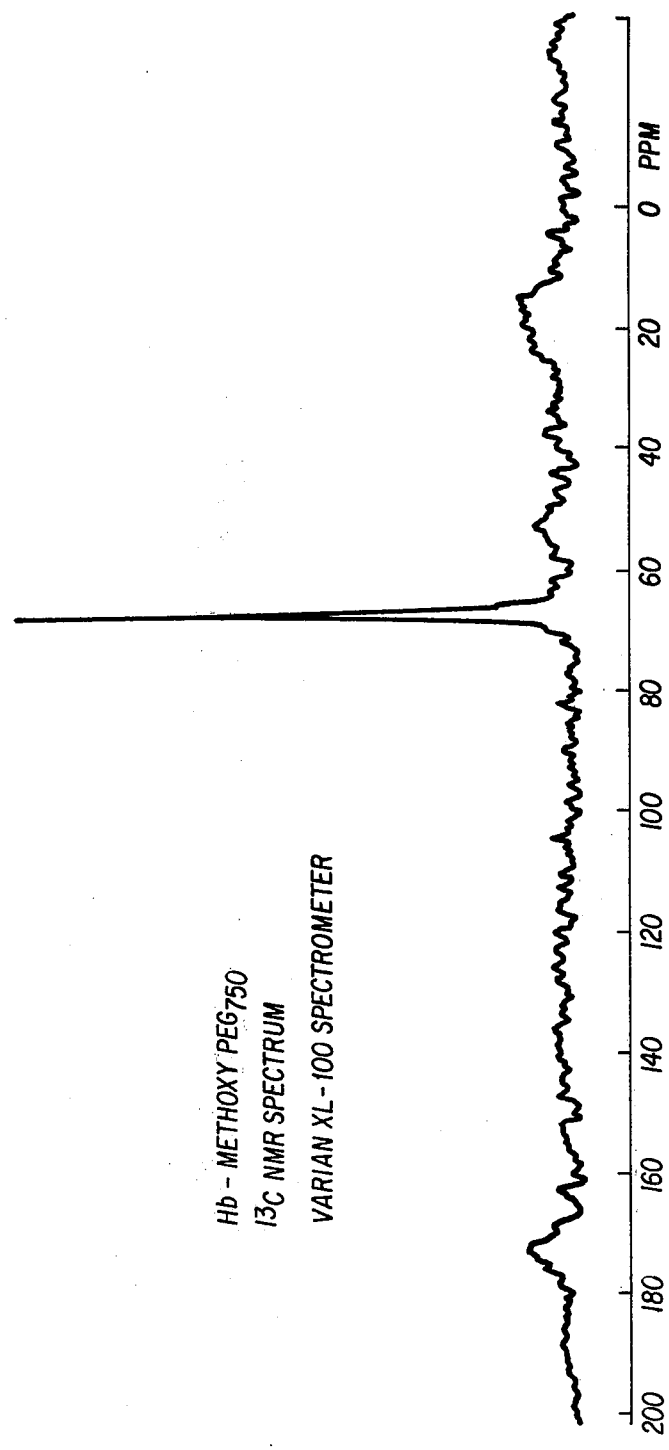

The modified hemoglobin is easily soluble in water, and color of the solution is red. A visible spectrum of the modified hemoglobin consisting of human hemoglobin and polyethylene glycol of which molecular weight is about 4000, is shown in FIG. 1. A $^{13}C$ nuclear magnetic resonance spectrum of the modified hemoglobin consisting of human hemoglobin and methoxy polyethylene glycol of which molecular weight is about 750, is shown in FIG. 2.

The modified hemoglobin is a nontoxic material, and the reason is that the modified hemoglobin is a combined matter of hemoglobin separated from a living body and the polymers employed in the invention which are highly nontoxic. Since oxygen affinity of the modified hemoglobin is nearly equal to or slightly stronger than that of natural hemoglobin, the modified hemoglobin is preferable for carrying oxygen to tissues. Furthermore, the residence time of the modified hemoglobin in the circulation is about 2–4 times longer than that of stroma free hemoglobin itself. As described above, the modified hemoglobin is preferable material for a blood substitute. In particular, it is known that a protein modified by polyethylene glycol loses the antigenicity of the protein (A. Abuchowski et al., J. Biol. Chem., vol. 252, p 3582 (1977)), and accordingly, there is no fear for the modified hemoglobin to act as antigen in the body. The number of polyalkylene glycol attached to hemoglobin described in the Examples was determined as follows: The concentration (Co) of a modified Hemoglobin solution was determined by the cyanomethemoglobin method, and the weights of the modified hemoglobin (Mo) was measured after freeze-drying of $v_0$ ml of the solution. Thus, the number of polyalkylene glycol (N) is:

$$N = \frac{\frac{m_o - C_o V_o}{M_1}}{\frac{C_o V_o}{M_2}},$$

where $M_1$ and $M_2$ are the molecular weights of polyalkylene glycol and hemoglobin, respectively.

EXAMPLE 1

2.5 Grams (0.003 mole) of polyethylene glycol monomethyl ether of which the mean molecular weight is 750 were dissolved in 40 ml water, and 1 g (0.0095 mole) of cyanogen bromide which was previously dissolved in 5 ml dioxane was added dropwise to the aqueous solution while the solution was chilled in an ice bath. Then, the mixture was stirred for one hour, while the mixture was maintained in the range of pH 9 to 10 using 2 N NaOH. The mixture was adjusted to pH 7.5 using 1 N HCl and concentrated to 20 ml by ultrafiltration using G-05T membrane (made by Bioengineering Co., Ltd.) of which cut-off molecular weight is 500 dalton. The concentrate was diluted with 300 ml of phosphate buffer solution of pH 7.5, and then concentrated to 20 ml by the ultrafiltration again. 20 ml of 10% aqueous solution of human hemoglobin were added to the concentrate while the concentrated solution was stirred and chilled in an ice bath. The reaction mixture was then allowed to stand overnight at 4° C. Subsequently, the reaction mixture was passed through a column where CM-Sephadex gel was packed and pre-equilibrated to pH 6.0. The column was eluted with 0.05 M phosphate buffer solution of pH 6.8 and the fractions of the modified hemoglobin were collected. The fractions were desalted and concentrated by ultrafiltration using A-15T membrane of which cut-off molecular weight is 15000 dalton. The concentrate was filtered through a 0.45μ membrane, and the filtrate contained 3.5 g of a combined material of hemoglobin and polyethylene glycol monomethyl ether as a dried matter. About 10 molecules of polyethylene glycol monomethyl ether were combined with one hemoglobin molecule.

EXAMPLE 2

7.2 Grams (0.01 mole) of polyethylene glycol monomethyl ether of which the mean molecular weight is 750 were dissolved in 500 ml benzene, and 10 g of sodium carbonate were added to the solution. 5.5 Grams (0.03 mole) of cyanuric chloride was added to the solution while it was cooled in an ice bath and vigorously stirred. The reaction mixture was vigorously stirred overnight at room temperature. The precipitate was filtered off, and 1 l of petroleum ether (b.p. 30°–70° C.) was added to the filtrate. Precipitate of 2-O-methoxypolyethylene glycol-4,6-dichloro-S-triazine (activated polyethylene glycol) was separated, and washed sufficiently with petroleum ether. The dry amount of the activated polyethylene glycol was 11.5 g. 0.5 Gram (0.0077 mmol.) of hemoglobin was dissolved in 100 ml of borate buffer solution of pH 9.2, and 1.7 grams (1.8 mmol.) of the dry activated polyethylene glycol were added to the solution while it was cooled in an ice bath. The mixture was stirred for one hour in an ice bath, and ultrafiltration using PM-30 membrane (made by Amicon Co.) was repeated twice, and thereby the remaining hemoglobin and activated polyethylene glycol were removed. The residue contained 2.1 g of the modified hemoglobin as a dried matter. About 50 molecules of polyethylene glycol monomethyl ether were combined with one hemoglobin molecule.

EXAMPLE 3

19 Grams (0.01 mole) of polyethylene glycol monomethyl ether of which the mean molecular weight is 1,900 were activated using 400 ml of benzene, 10 g of sodium carbonate and 5.5 g (0.03 mole) of cyanuric chloride in the same manner as employed in Example 2, and accordingly, 24 g of the activated polyethylene glycol were obtained. 6.4 Grams (3.1 mmol.) of the activated polyethylene glycol so produced were treated with 2 g (0.031 mmol.) of hemoglobin and 200 ml of borate buffer solution of pH 9.2 in the same manner as Example 2, and 5.6 g of the modified hemoglobin were obtained. About 57 molecules of polyethylene glycol monomethyl ether were combined with one hemoglobin molecule.

EXAMPLE 4

50 Grams (0.01 mole) of polyethylene glycol monomethyl ether of which the mean molecular weight is 5,000 were activated using 500 ml of benzene, 10 g of sodium carbonate and 5.5 g (0.03 mole) of cyanuric chloride in the same manner as Example 2, and accordingly, 53 g of the activated polyethylene glycol were obtained. 40 Grams of the activated polyethylene glycol so produced were treated with 20 ml of 10% hemoglobin solution and 450 ml of borate buffer solution of pH 9.2 in the same manner as Example 2, and 14 g of the modified hemoglobin were obtained. About 75 molecules of polyethylene glycol monomethyl ether were combined with one hemoglobin molecule.

EXAMPLE 5

40 Grams (0.002 mole) of polyethylene glycol of which the mean molecular weight is 20,000 were mixed with 1 l of benzene, 10 g of sodium carbonate and 1.1 g (0.006 mole) of cyanuric chloride, and the mixture was stirred overnight at room temperature. 1 Liter of petroleum ether was added to the mixture, and precipitate formed was treated according to the same manner as employed in Example 2 to obtain 39 g of activated polyethylene glycol. 10 Grams (0.0005 mole) of the above activated polyethylene glycol were added to the mixture of 20 ml (0.00003 mole) of 10% hemoglobin and 400 ml of borate buffer solution of pH 9.2 which was previously cooled in an ice bath, and then stirred for one hour. The reaction mixture was concentrated by ultrafiltration using XM-100 membrane (made by Amicon Co.) and the modified hemoglobin in the reaction mixture was adsorbed on a column of CM-Sephadex gel which was pre-equilibrated with 0.05 M phosphate buffer solution of pH 6.0. The first fraction of elution using pH 6.3 phosphate buffer solution discarded, and the next fraction using pH 6.8 phosphate buffer solution was collected. The fraction was concentrated by using the XM-100 membrane, and 3 g of the modified hemoglobin were obtained as a dried matter. About 4 molecules of polyethylene glycol were combined with one hemoglobin molecule.

EXAMPLE 6

Using 12.5 g (0.005 mole) of polyethylene glycol monostearyl ester of which the mean molecular weight is 2,500, 400 ml of benzene, 5 g of sodium carbonate and 2.75 g (0.015 mole) of cyanuric chloride, the same treatment as Example 2 was carried out, and accordingly 13.5 g of activated polyethylene glycol were obtained. 10.5 Grams (0.004 mole) of the above activated polyethylene glycol were treated with 25 ml (0.04 mmol.) of 10% hemoglobin solution and 900 ml of borate buffer solution of pH 9.2 in the same manner as Example 2, and 8 g of the modified hemoglobin were obtained. About 52 molecules of polyethylene glycol monostearyl ester were combined with one hemoglobin molecule.

EXAMPLE 7

Using 5 g (0.005 mole) of polyethylene glycol monooleyl ether of which the mean molecular weight is 1,000, 400 ml of benzene, 5 g of sodium carbonate and 2.75 g (0.015 mole) of cyanuric chloride, the same treatment as Example 2 was carried out, and accordingly 6 g of activated polyethylene glycol were obtained. 5.3 Grams (0.002 mole) of the above activated polyethylene glycol were treated with 1.3 g (0.02 mmol.) of bovine hemoglobin (made by Sigma Co.) and 450 ml borate buffer solution of pH 9.2 in the same manner as Example 2, and 4.2 g of the modified hemoglobin were obtained. About 85 molecules of polyethylene glycol monooleyl ether were combined with one hemoglobin molecule.

EXAMPLE 8

12 Grams (0.003 mole) of polypropylene glycol of which the mean molecular weight is 4,000 were dissolved in 120 ml water. Using 0.0095 mole of cyanogen bromide, the solution was treated in the same manner as Example 1, and accordingly a concentrate of ultrafiltration was obtained. Using 2 g of porcine hemoglobin (made by Sigma Co.), the concentrate was treated in the same manner as Example 1, and accordingly 7 g of the modified hemoglobin were obtained. About 15 molecules of polypropylene glycol were combined with one hemoglobin molecule.

EXPERIMENT

The residence time in a blood vessel and oxygem affinity of the modified hemoglobins were measured.

Two rats having an average weight of 350 g were employed as a sample. The rats were injected with 5 ml of 4–6% modified hemoglobin per kg of body weight of rat through a femoral vein, and each 0.5 ml of blood was withdrawn at 5, 10, 15, 30, 60, 90 and 120 minutes after the injection. Each blood sample was centrifuged, and the concentration of the modified hemoglobin in the plasma was determined by the cyanomethemoglobin spectral method. The data were plotted on a graph, and the half-life residence time of the injected modified hemoglobin in the plasma was determined from the graph.

TABLE 1

| | Hemoglobin | Half-life residence time |
|---|---|---|
| The material of the invention | The modified hemoglobin of Example 1 | 150 minutes |
| | The modified hemoglobin of Example 2 | 120 minutes |
| | The modified hemoglobin of Example 3 | 110 minutes |
| | The modified hemoglobin of Example 4 | 210 minutes |
| Control | Natural hemoglobin | 50 minutes |
| | Polyhemoglobin of Japanese Patent Publication No. 76-63920 | 100 minutes |

TABLE 1-continued

| Hemoglobin | Half-life residence time |
|---|---|

As to the modified hemoglobin solution (0.1 M NaCl solution, pH 7.40), the oxygen partial pressure at which the hemoglobin is half saturated with oxygen ($P_{50}$-value) was determined by oxygen dissociation curve which was measured by using the apparatus reported by Imai et al (K. Imai, H. Morimoto, M. Kotani, H. Watari, H. Waka and M. Kuroda, Biochem. Biophys. Acta., Volume 200, 189–196 (1970)). The date are shown in Table 2.

TABLE 2

| | Hemoglobin | $P_{50}$ |
|---|---|---|
| The material of the invention | The modified hemoglobin of Example 2 | 13.5 mmHg |
| | The modified hemoglobin of Example 3 | 15.0 |
| | The modified hemoglobin of Example 5 | 19.5 |
| Control | Natural hemoglobin | 15.0 |
| | Polyhemoglobin of Japanese Patent Publication No. 76-63920 | 9.0 |
| | Dextran-Hemoglobin of Japanese Patent Publication No. 77-51016 | 10.0 |

What is claimed is:

1. An oxygen carrying material which comprises hemoglobin attached by a chemical reaction to a polymer selected from the group consisting of polyethylene glycol, polypropylene glycol, a copolymer of ethylene glycol with propylene glycol, an ether of one of the above polyethylene glycols with an alcohol having a carbon number of 1 to 16, an ester of one of the above polyalkylene glycols with a carboxylic acid having a carbon number of 2 to 18, and a dehydrated product of one of the above polyalkylene glycols with an amine having a carbon number of 1 to 18.

2. The material of claim 1 wherein said polymer has a molecular weight of 300–20,000.

3. The material of claim 2 wherein said molecular weight is 750–5,000.

4. The material of claim 1 wherein said hemoglobin and said polymer are attached to each other directly.

5. The material of claim 1 wherein said hemoglobin and said polymer are attached to each other by means of a cross-linking agent.

6. In a method of carrying oxygen to an animal tissue by means of an oxygen carrier, the improvement which comprises using as an oxygen carrier the attached hemoglobin polymer material of claim 1.

7. The material of claim 1 wherein said attachment of said hemoglobin to said polymer occurs by reacting said hemoglobin with said polymer which has been pretreated with cyanogen bromide.

* * * * *